United States Patent [19]

Reymond et al.

[11] Patent Number: 5,500,358
[45] Date of Patent: Mar. 19, 1996

[54] ANTIBODY CATALYSIS OF CYCLOHEXADIENONE REARRANGMENTS

[75] Inventors: Jean-Louis Reymond, Del Mar; Yuanwei Chen, San Diego; Richard A. Lerner, La Jolla, all of Calif.

[73] Assignee: The Scripps Research Institute, La Jolla, Calif.

[21] Appl. No.: 292,934

[22] Filed: Aug. 18, 1994

[51] Int. Cl.$^6$ .................... C12P 7/22; C12N 9/00
[52] U.S. Cl. ................ 435/156; 435/188.5; 435/240.26; 435/240.27
[58] Field of Search ............... 435/188.5, 240.26, 435/240.27, 156

[56] References Cited

PUBLICATIONS

Hart, et al., "Synthesis of 6H–DiBenzo[b,d]Pyran–6–Ones Via Dienone Phenol Rearrangements of Spiro[2,5–Cyclohexadiene–1,1' (3+H)–Iso Benzofuran]–3'–Ones", *Tetrahedron*, 48: 8179–8188 (1992).
Miller, B., "Too Many Rearrangemetns of Cyclohexadienones", *Accounts of Chemical Research*, 8: 245–256 (1975).
Valderrama, et al., "Studies on Quinones. XV. A Convenient Entry Into the Tetrahydrophenanthrene–1,4–Quinone System Utilizing the Dienone–Phenol Rearrangement of Spiro [Cyclo Pentanenaphthalene]Triones", *Tet. Lett.*, 26: 6281–6284 (1985).

*Primary Examiner*—Charles L. Patterson, Jr.
*Attorney, Agent, or Firm*—Donald G. Lewis

[57] ABSTRACT

Catalytic antibodies are employed for catalyzing rearrangement reactions involving carbon-carbon bonds. The catalytic antibodies are generated using haptens that are transition state analogs of the such rearrangement reactions. More particularly, the haptens dispslay an electrostatic complementarity with the transition state. Since the formation of a transient positive charge in the migrating bond is a general feature of nucleophilic 1,2-shifts, it is disclosed that haptens for generating catalytic antibody directed to such reactions must incorporate such charge. Antibody catalysis of the dienone-phenol rearrangement is shown to catalyze both the hydronium ion promoted pathway and the spontaneous rearrangement pathway, indicating that the antibody stabilizes the localized positive charge of the transition state.

13 Claims, 3 Drawing Sheets

ANTIBODY CATALYSIS OF CYCLOHEXADIENONE REARRANGMENTS

GOVERNMENT RIGHTS

This invention was made, in part, with government support under Grant No. GM 49736. The U.S. government may have certain rights in the invention.

FIELD OF INVENTION

The invention relates to a catalytic antibodies and to their generation and use. More particularly, the invention relates to catalytic antibodies employable for catalyzing nucleophilic 1,2-shifts of carbon-carbon bonds, including dienone-phenol rearrangements.

BACKGROUND

Many rearrangements of carbon-carbon bonds are nucleophilic 1,2-shifts in which an electronic sextet formed on an atom (A) attached to a carbon atom induces an adjacent carbon-carbon bond to move with its electron pairs to that center to fill its valence, leaving behind a carbenium ion. The carbenium ion is then stabilized by donation of an electron pair from one of its substituents. The general mechanism for a nucleophilic 1,2-shift of a carbon-carbon bonds is illustrated in Scheme 1:

Scheme 1

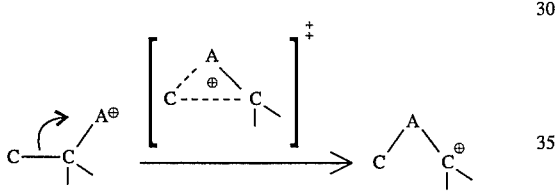

The above mechanism for nucleophilic 1,2-shifts of carbon-carbon bonds is of extremely broad scope and encompasses many important synthetic transformations. When A is a carbon, the reaction is a rearrangement such as the pinacol, the Wagner-Meerwein or the dienone-phenol reaction. The dienone-phenol reaction is illustrated in Scheme 2.

Scheme 2

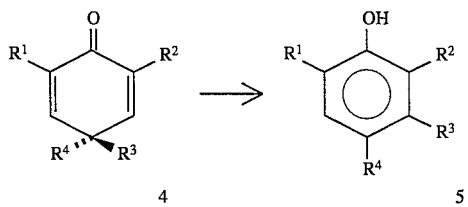

The dienone-phenol rearrangement is a acid catalyzed transformation of a 4,4-disubstitued cyclohexadienone into a 3,4-disubstituted phenol. Applied examples of the dieone-phenol rearrangement reaction are provided by R. Cassis, et al, *Tetrahedron Lett.* (1985), vol. 26, page 6281, by F. Hauser et al. in *J. Org. Chem.* (1978), vol. 431, page 113, by S. Kupchan et al. in *Heterocycles* (1976), vol. 4, page 235, by U. Eder et al. in *Chem. Ber.* (1978), vol. 111, page 939, and by D. Hart et al. in *Tetrahedron* (1992), vol. 48, page 8179. The acid catalyzed mechanism for the dienone-phenol rearrangement reaction for compound 7 is illustrated in FIG. 2. In the case of compound 7, the benzyl group migrates preferentially to give phenol 8. The reaction mechanism involves pre-equilibrium protonation of the carbonyl by the acid catalyst to form intermediate 10, followed by a rate determining migration of the benzyl group to form intermediate 12. Proton abstraction from position C(3) finally leads to aromatization and regeneration of the acid catalyst.

Cyclohexadienones are members of a class of molecules known as blocked aromatic molecules. Blocked aromatic molecules are molecules having a six membered carbon ring, five of the six ring carbons being conjugated by means of linear or cross-conjugation, one of the five conjugated ring carbons including a reducible substituent, and the remaining sixth unconjugated ring carbon including disubstitutions with at least one substituent being susceptible to a sigmatropic shift, i.e., a migrating substituent. Blocked aromatic molecules can undergo aromatization by means of skeletal rearrangements involving 1,2-, 1,3-, 1,4-, 1,5-, 3,3-, 3,4-, 3,5-, or 5,5- sigmatropic shifts. Representative members of the class of blocked aromatic molecules include disubstituted cyclohexadienones, methylene-cyclohexadienes (semibenzenes), and cyclohexadienyl carbenes, illustrated in Scheme 3 below:

Scheme 3

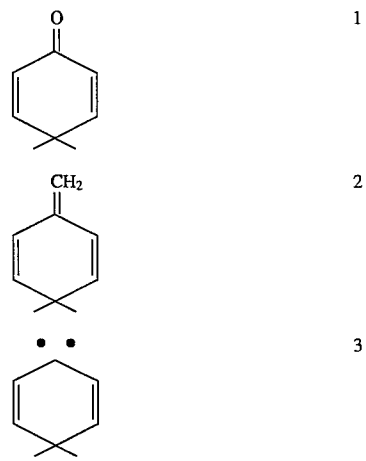

Amongst the various class members indicated above, cyclohexadienones are generally the least susceptible to skeletal rearrangements. The driving force for aromatizing cyclohexadienones is tempered by the greater relative stability of their carbonyl structures over their corresponding enol structures. As a rule, however, all blocked aromatic molecules more readily undergo skeletal rearrangements to achieve aromatization as compared to corresponding acyclic analogs because the transition states of blocked aromatic molecules attain a higher degree of aromatic character.

Cyclohexadienones may undergo thermal (spontaneous) or acid-catalyzed rearrangements. Acid catalyzed rearrangements of 4,4-disubstituted cyclohexadienones (para cyclohexadienones) involve a three step reaction mechanism, illustrated in FIG. 2. Initially, the carbonyl group of the 4,4-disubstituted cyclohexadienone undergoes a protonation by the acid catalyst resulting in a partial transfer of charge to the conjugated ring carbons. The protonation of the carbonyl group is then followed by a rate determining 1,2-shift of a substituent from the C(4) ring position to the C(3) ring position via a transition state. The transition state includes a three membered ring involving the migrating substituent, the C(3) ring carbon and the C(4) ring carbon. The transition state is stabilized by a partial localization of charge onto this three membered ring. After completion of the 1,2- shift, aromatization is completed by abstraction of the proton from the C(3) ring position and regeneration of the acid catalyst. The reaction mechanism of corresponding thermal or spontaneous rearrangements do not include an intermediate in which the carbonyl group is protonated.

There are several species of migrating substituents disclosed in the prior art, e.g., benzyl substituents, allyl substituents, and alkyl substituents. All three species have been shown to participate as migrating groups within dienone-phenol rearrangement reactions and are reviewed by B. Miller in *Account. Chem. Res.* (1975) vol. 8, pages 245–256. Benzyl substituents are generally observed to more readily undergo a 1,2- shift in a dienone-phenol rearrangement reaction. Allyl groups are highly migratory and can undergo a 1,2- shift in a dienone-phenol rearrangement reaction but are also known to undergo 3,3- shifts. Alkyl substituents are generally slower migrators than allyl or benzyl substituents.

Although rearrangement reactions involving cyclohexadienones are chemically important, many migrating species are slow and thereby limit their applicability. Energy barriers for sigmatropic shifts can be relatively high. What is needed is a stereospecific method for catalyzing cyclohexadienone rearrangements.

It is known that catalytic antibodies can be generated by inoculating an immune responsive animal with a stable transition state analog of the chemical reaction sought to be catalyzed. This technique provides a rapid and practical entry into new protein catalysts and has been successfully applied to a number of chemical tranformations, e.g., R. A. Lerner et al., *Science* (1991), vol. 252, pages 659–667 and P. G. Schultz et al., *Acc. Chem. Res.* (1993), vol. 26, page 391. However, only a few reactions involving carbon-carbon bonds have been catalyzed by antibodies. Such reactions have been reviewed by D. Hilvert in *Acc. Chem. Res.* (1993), vol. 26, page 552. Generation of catalytic antibody for catalyzing the Diels-Alder reaction is disclosed by D. Hilvert et al. in *J. Am. Chem. Soc.* (1989), vol. 111, page 9261, by A. C. Braisted et al. in *J. Am. Chem. Soc.* (1990), vol. 112, page 7430, and by V. Grouverneur et al. in *Science* (1993), vol. 262, page 204. Generation of catalytic antibody for catalyzing the Cope rearrangement reaction is disclosed by D. Hilvert et al. in *J. Am. Chem. Soc.* (1988), vol. 110, page 5593, by B. Jackson et al. in *J. Am. Chem. Soc.* (1988), vol. 110, page 4841, and by D. Jackson et al. in *Angew. Chemie Int. Ed. Engl.* (1992), vol. 31, page 182. Generation of catalytic antibody for catalyzing decarboxylation reactions is disclosed by C. Lewis et al. in *Science* (1991), vol. 253, page 1019, by J. A. Ashley, et al. in *J. Am. Chem. Soc.* (1993), vol. 115, page 2515. However, no one has reported the generation of a catalytic antibody for catalyzing nucleophilic 1, 2-shifts of carbon-carbon bonds in general or of the dienone-phenol rearrangement reaction in particular.

SUMMARY

The invention is directed to antibody molecules having catalytic activity for catalyzing a dienone-phenol rearrangement reaction, i.e., for catalytically coupling an aromatization of a blocked aromatic molecule with a sigmatropic shift of a migratory substituent on such blocked aromatic molecule. A blocked aromatic molecule is defined herein to be molecule which includes a nonaromatic six membered carbon ring having five conjugated carbons and one unconjugated carbon. One of the five conjugated carbons must include a reducible substituent. The unconjugated carbon must include a disubstitution, at least one of the disubstitutions being a migratory substituent susceptible to a sigmatropic shift upon such six membered carbon ring. Optionally, selected conjugated carbons may include substituents, including alkyl substituents, which block sigmatropic shifts to such positions.

The catalytic antibody molecules of this invention include an antibody combining site portion and are identifiable, in part, by the binding affinity of such antibody combining site portion. In particular, the antibody combining site portion of catalytic antibodies have a binding specificity for blocked aromatic molecules and for haptenic piperidinium cations having a ring nitrogen with the same disubstituents found on the blocked aromatic molecule, or analogs of such disubstituents. The binding affinity is determined in aqueous solution at physiological pH. In an alternative embodiment, the antibody combining site portion of the catalytic antibody is incorporated into a larger molecule while retaining its defining catalytic and binding functions.

In a preferred embodiment, the invention is directed to antibody molecules which catalyze rearrangement reactions of para disubstituted cyclohexadienones, wherein at least one of the disubstituents is a migratory substituent, i.e., dienone-phenol rearrangement reactions. Preferred migratory substituents include benzylic substituents, allyl substituents, and alkyl substituents. A preferred catalytic antibody is the antibody molecule secreted by hybridoma 62C7 having ATCC accession number HB11703.

The invention is also directed to cells, preferably hybridoma cells, that, when cultured in a culture medium, produce monoclonal antibody molecules or molecules containing antibody combining site portions that catalyze a dienone-phenol rearrangement reaction, as indicated above. A preferred exemplary hybridoma cell line, denominated 62C7, was deposited at the American Type culture Collection, 12301 Parklawn Drive, Rockville, Md. This hybridoma was deposited on August 17, 1994 and received accession number HB 11703. This deposit was made in compliance with the Budapest Treaty requirements that the duration of the deposits should be for 30 years from the date of deposit or for 5 years after the last request for the deposit at the depository or for the enforceable life of a U.S. patent that matures from this application, whichever is longer. The hybridoma will be replenished should it become nonviable at the depository. The hybridoma will be freely available upon request to the public upon issuance of a United States patent.

The invention is also directed to a method for catalyzing a dienone-phenol rearrangement reaction, i.e., for catalytically coupling the aromatization of blocked aromatic molecules with a sigmatropic shift of a migratory substituent on such blocked aromatic molecule. The method employs an admixing step in which a catalytically effective amount of the catalytic monoclonal antibody molecules or paratope-containing portions of such monoclonal antibodies is combined in an aqueous medium with a blocked aromatic molecule, e.g., para disubstituted cyclohexadienones, to form a reaction admixture. In the preferred mode, the aqueous medium has a pH value of between about 5 and 8. The admixing step is then followed by an incubation step in which the reaction admixture is maintained for a period of time sufficient for the catalytic antibody molecules or molecules containing antibody combining site portions thereof to bind the aromatic molecule and catalyze the dienone-phenol rearrangement reaction or more generally, for catalyzing the coupling of the aromatization of the blocked aromatic molecule with a sigmatropic shift of a migratory substituent upon such blocked aromatic molecule.

The invention is also directed to a method for preparing cells that, when cultured in a medium, produce the catalytic antibody molecules described above. The process for producing hybridomas is initiated by immunizing an animal with an immunogen that includes a piperidinium cation having a disubstituted ring nitrogen. The immunized animal is then maintaining for a time period sufficient for such animal to secrete antibodies that immunoreact with a haptenic piperidinium cation. The genes that encode antibody molecules or molecules containing antibody combining site portions from antibody-producing cells of the immunized animal of the prior step are transferred into host cells to form hybrid cells that contain genes from at least two sources, i.e., to form hybridoma cells. The formed hybrid cells (i) produce antibody molecules or molecules containing antibody combining site portions from said transferred genes when cultured and (ii) can be cultured substantially indefinitely. Culturing the hybrid cells in as appropriate culture medium for a time period sufficient cells to produce antibody molecules or molecules containing antibody combining site portions. Antibody molecules or molecules containing antibody combining site portions are recovered from the cultured hybrid cells. The obtained antibody molecules are screened to obtain antibody molecules or molecules containing antibody combining site portions that catalyze the dienone-phenol rearrangement reaction. Clones of said identified hybrid cell are then grown in culture to produce antibody molecules or molecules containing antibody combining site portions that catalyze the dienone-phenol rearrangement reaction.

DETAILED DESCRIPTION

Figure 1:
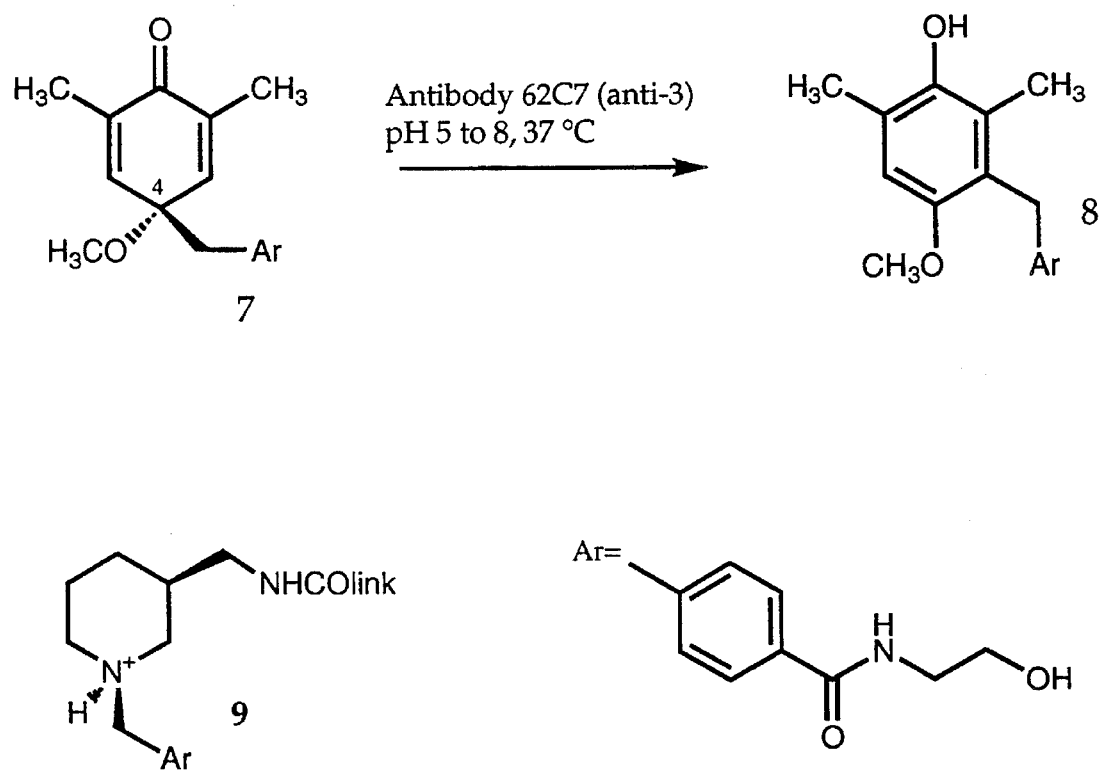
FIG. 1 illustrates an example of the catalysis of a dienone-phenol rearrangement reaction by catalytic antibody 62C7, i.e., the aromatization of compound 7 and the benzylic migratory group from the C(4) position to the C(3) position to form compound 8. Compound 9 is the haptenic piperidinium cation employed to generate catalytic antibody 62C7.
Figure 2:
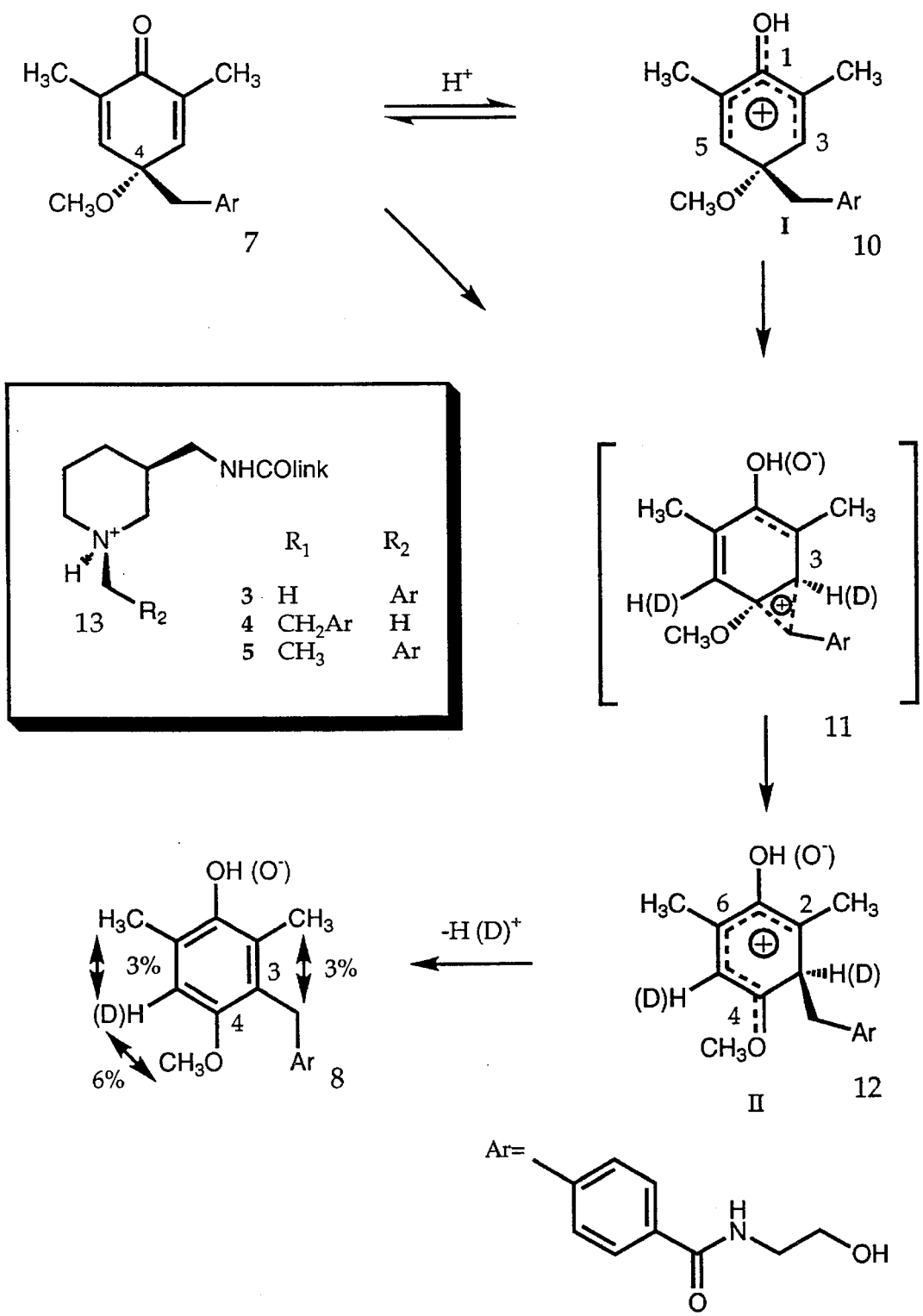
FIG. 2 illustrates the proposed mechanism of the dienone-phenol rearrangement reaction presented in FIG. 1, indicating reaction intermediates 10 and 12 and transition state 11. Compound 8 illustrates the nuclear Overhauser effect (NOE) effects and confirms that the benzylic group migrated to position C(3).

The invention employs transition state analogs of the dienone-phenol rearrangement reaction as a hapten for generating catalytic antibody. As illustrated in FIG. 2, two important structural and electronic changes occur during the dienone-phenol rearrangement as a result of the benzyl group migration. Firstly, carbons C(3) and C(4) change their hybridization, passing through a three membered ring structure at the transition state, e.g., compound 11. Secondly, the positive charge, which is delocalized at positions 1,3, and 5 and on the carbonyl in intermediate 10, becomes localized in the rearranging C-C bond. It is demonstrated herein that piperidinium haptens, e.g., compounds 13.3, 13.4 and 13.5, are transition state analogs of the dienone-phenol rearrangement reaction and that these compounds can serve as haptens for generating catalytic antibody directed to catalyzing the dienone-phenol rearrangement reaction. Piperidinium haptens mimic the charge distribution at the transition state by displaying an ammonium center in the homobenzylic position of the migrating aromatic group. Antibodies generated against these compounds are candidates for having catalytic activity directed to the rearrangement of 7 to 8.

EXAMPLE

Dienone 7 was employed as a substrate for an antibody catalyzed dienone-phenol rearrangement reaction. Dienone 7 was obtained as a minor product in the alkylation of 4-methoxy-2,6-dimethyl phenol. Firstly, 4-methoxy-2,6-dimethyl phenol was obtained in 87% yield by reaction of 2,6-dimethyl hydroquinone with concentrated $H_2SO_4$ in refluxing methanol according to the method of H. Greuter et al. *Helv. Chim. Acta* (1972), vol. 55, page 2382. 4-Methoxy-3,5-dideutero-2,6-dimethyl phenol was obtained using $D_2SO_4$ and methanol-$d_1$ with 96% d-incorporation, 85% yield. Treatment of the above intermediates with N-hydroxyethyl-4 -chloromethyl benzamide and sodium hydroxyde in refluxing water produced dienone 7 with a 2.5% yield, according to the method of J. Borgulya et al., *Helv. Chim. Acta* (1973), vol. 56, page 34. Other products included the O-alkylation product (38%) and the 2-alkylation product (25%). Compound 7 was purified by preparative HPLC with greater that 98% purity using reverse-phase C-18 with an $H_2O$—$CH_3CN$ gradient.

Compound 7 was characterized by selected physical properties, viz.:

m.p.130.0°–131.0° C., $^1$H–NMR (500MHz, $CDCl_3$):7.66, 7.16 (2xd,$^3$J=8.2 Hz,2x2H), 6.88 (t,$^3$J=5.3 Hz, 1H), 6.45 (s,2H), 3.78 (t,$^3$J=4.7 Hz, 2H), 3.58 (dt,$^3$J=4.7 Hz, 5.3 Hz, 2H), 3.15 (s, 3H), 2.97 (s, 2H), 1.84 (s, 6H); $^{13}$C–NMR (125 MHz, $CDCl_3$): 186.4, 168.3, 145.4, 139.5, 137.9, 132.5, 130.8, 126.5, 75.4, 62.1, 52.8, 46.3, 42.7, 15.8, 15.7; Selected physical properties of 2: m.p. 147.0°–148.0° C. $^1$H–NMR (500 MHz, $CD_3CN$): 7.66, 7.16 (2xd,$^3$J=8.3 Hz, 2x2H), 7.08 (bs, 1H), 6.67 (s, 1H), 5.64 (s, 1H), 4.03(s, 2H), 3.70 (s,3H), 3.59(m, 2H), 3.41 (m, 2H), 3.15 (t, $^3$J=4.5 Hz, 1H), 2.21,2.06 (2xs, 2x3H); $^{13}$C–NMR (125 MHz, $CD_3CN$): 168.6, 152.1, 147.6, 146.2, 132.8, 129.1, 128.0, 126.1, 125.7, 123.8, 112.0, 61.6, 56.6, 43.1, 32.2, 17.0, 12.9.

When treated with aqueous acid, dienone 7 was quantitatively converted to phenol 8.

Hapten 13.3 was obtained in an eight step synthesis starting from 3-hydroxymethylpiperidine and 4-(chloromethyl)-N-(2'-hydroxyethyl)benzamide accordingly to the method of J.-L. Reymond et al, *Angew. Chem. Int. Ed. Engl.* (1991), vol. 30, page 1711. In a similar fashion, a 1:1 mixture of diastereoisomeric haptens 13.4 and 13.5 was obtained starting with N-methyl-3hydroxymethylpiperidine. Haptens 13.4 and 13.5 were then separated by reverse phase high performance liquid chromatography using a semipreparative RP-HPLC C-18 column with 0.1% $HCl/H_2O$ at a rate of 1 milliliter/minute. The retention time for hapten 13.4 was $t_R=15.0$ minutes. The retention time for hapten 13.5 was $t_R=15.7$ minutes. The relative configuration was assigned on the basis of the $^1$H NMR spectrum of hapten 13.4 using the nuclear Overhauser effects (NEO), $D_2O$, 500 MHz. Irradiation of the $CH_3$—$N^+$signal affected the piperidine ring protons $H_{eq}C(2)+H_{eq}C(6)$ (2.6%), $H_{ax}C(6)$ (4.5%) and $H_{ax}C(2)$ (4.5%). Irradiation of the signal at δ=4.6

(Ar—CH—N$^+$) affected H$_{eq}$C(2)+H$_{eq}$C(6) (2.1%), H$_{ax}$C(3) (2.8%) and H$_{ax}$C(5) (2.1%).

A linker was attached to haptens 13.3, 13.4, and 13.5 to insure immunogenicity. The haptens were activated with (5-[(2,5-dioxo-1-pyrrolidinyl) oxy]-5-oxopentanoyl chloride, Et (iPr)$_2$N, dimethylformamide (DMF) at −30° C. The activated haptens were then coupled to the carrier proteins bovine serum albumin (BSA) and keyhole limpet hemocyanin (KLH).

TABLE 1

Isotopic Effects on Antibody Catalyzed and Background Rearrangements of 7 to 8

| Substrate | pH | Km, μM | $k_{cat}$ s$^{-1}$ | $k_{uncat}$ s$^{-1}$ | $k_{cat}/k_{uncat}$ |
|---|---|---|---|---|---|
| 7 | 5.75 | 670 | 1.22 × 10$^{-6}$ | 1.51 × 10$^{-8}$ | 80 |
| 7-d$_2$ | 5.75 | 770 | 1.37 × 10$^{-6}$ | 1.71 × 10$^{-8}$ | 80 |
| 7 | 7.07 | 1200 | 1.25 × 10$^{-6}$ | 1.38 × 10$^{-8}$ | 90 |
| 7 (D$_2$O) | 7.07 (pD) | 1300 | 1.25 × 10$^{-6}$ | 1.31 × 10$^{-8}$ | 95 |

The KLH conjugates of haptens 13.3, 13.4, and 13.5 were then employed to inoculate Balb/c mice and antibodies were generated by standard protocols. (G. Kohler et al. *Nature* (1975), vol. 265, page 495.) Monoclonal antibodies were purified from ascites fluid by anion exchange chromatography and assayed against substrate 7 for production of the phenol product 8. Fourteen anti-13.3, twenty two anti-13.4, and twenty one anti-13.5 antibodies were assayed for catalysis of the rearrangement reaction converting dienone substrate 7 to phenol product 8. One anti-13.3 and one anti-13.4 antibody were found to catalyze the reaction. As illustrated in Table 1, catalysis followed Michaelis-Menten kinetics. Assay condition employed 50–1500 μM antibody in 100 mM NaCl, 50 mM of either bistris(bis(hydroxyethyl)-tris(hydroxymethyl)aminomethane) or 1,3-bis[tris (hydroxymethyl)aminopropane at 37° C. Product formation was followed by reverse-phase HPLC (Vydac C-18 218TP54 column (0.45×22 cm) at a flow rate of 1.5 milliliters/minute using 28% CH$_3$CN and 72% H$_2$O+0.1% CF$_3$COOH. Retention time t$_R$ for substrate 7 was 5.02 minutes. Retention time t$_R$ for product 8 was 7.14 minutes. The pD (98%) D$_2$O values were obtained by adding 0.4 to the pH-electrode reading. It was also observed that rearrangement reactions were quantitatively inhibited by addition of the respective haptens, thereby ensuring that the observed catalytic reaction was taking place in the antibody combining site. Antibody 62C7 (anti-13.3) was characterized in detail.

Figure 3:
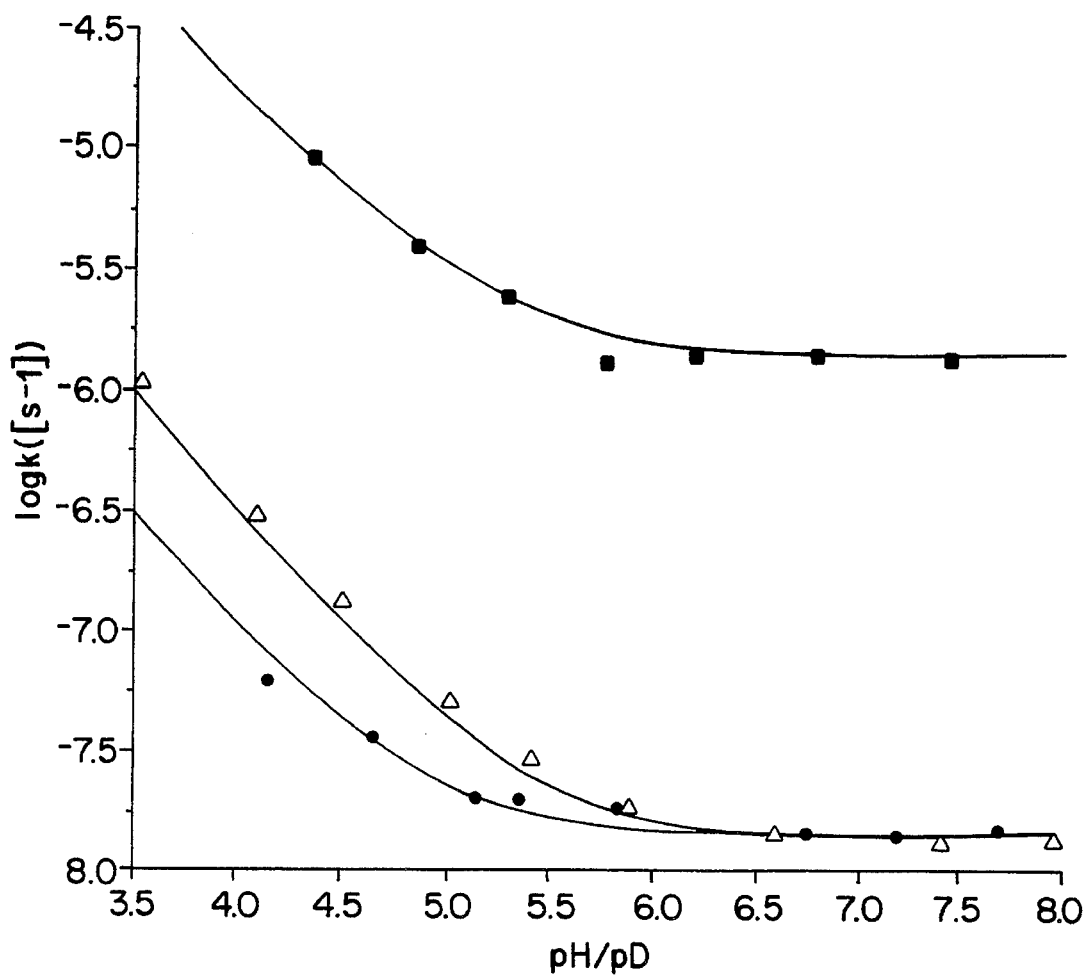
FIG. 3 illustrates the pH-profile for the dienone-phenol rearrangement reaction of FIG. 2. The pH-profile of the reaction catalyzed by antibody 62C7 (anti-3) is indicated by the solid boxes. The background pH-profile with respect to $H_2O$ is indicated by solid circles; the backgound pH-profile with respect to $D_2O$ is indicated by empty triangles.

FIG. 3 illustrates the pH-profile of the rearrangement reaction in the presence of catalytic antibody 62C7 (anti-13.3) and without. Background rates are determined in H$_2$O and in D$_2$O. The lines are caluclated from the following equations respectively:

$$k_{cat}=k_{cat}°+k_{catH^+}[H_3O^{3O}]^{0.92};\ k_{H2O}=k°+k_H^+[H_3O^{3O}];\ k_{D2O}=k°+k_{D^+}[D_3O^+].$$

Accordingly, FIG. 3 illustrates both the antibody 62C7 catalyzed and the background reactions proceed via a hydronium ion catalyzed pathway, viz. k$_{catH+}$=0.176/Mole second, $_{H+}$=1.51×10$^{-3}$/Mole second. The background reaction also exhibits a large, inverse solvent isotope effect, viz., k$_{H+(H2O)}$/k$_{H+(D2O)}$=0.32. This is consistent with pre-equilibrium protonation of substrate 7 to form a first intermediate 10. This reaction probably reflects the spontaneous rearrangement of substrate 7 to the conjugate base of a second intermediate 12. This rearrangement reaction probably also occurs when substrate 7 is complexed with anti-13.3, i.e., second intermediate 12 is formed within the antibody complex. Importantly, a small inverse secondary isotope effect is observed in all cases at position C(3) of the dienone, viz., k$_{catH}$/k$_{catD}$=0.88 at pH=5.75, k$_H$/k$_D$=0.88–0.94 from pH=2.95 to 9.54. This indicates that the rate determining step involve rehybridization from sp$^2$ to sp$^3$ at the center. Accordingly, the rate determining step is the carbon-carbon and not the migration itself. (V. Vitullo et al., *J. Am. Chem. Soc.* (1974), vol. 94, page 3844.) Although this carbon hydrogen bond is ultimately broken to yield the product phenol 8, it is not involved in the rate determining step as this would have given rise to a large, normal isotope effect at that position.

The pH-profile and isotope effect studies above demonstrate that antibody 62C7 catalyzes both the hydronium ion promoted and the spontaneous rearrangement of substrate 7 to product 8 with similar efficiency without altering their mechanism. It is clearly not a simple acid catalyst. As both pathways involve localization of a positive charge in the rearranging C—C bond, 62C7 might achieve catalysis by selective stabilization of the charge distribution at the transition state 11, as compared to intermediate 10. Accordingly, antibody 62C7 is distinguished over other anti-13.3, 13.4, and 13.5 antibodies which may fail to catalyze the reaction by binding intermediate 10 equally or better than the transition state 11. The catalytic effect does not change significantly from pH 5 to pH 8. Stabilization of a positive charge could be mediated either by an antibody carboxylate residue with a pK$_a$ below 5 or by aromatic residues.

What is claimed is:

1. Antibody molecules or molecules containing antibody combining site portions that catalyze a coupling of an aromatization of a blocked aromatic molecule with a sigmatropic shift of a migratory substituent on said blocked aromatic molecule, said antibody molecules including an antibody combining site portion which, in aqueous solution at physiological pH values, binds to said blocked aromatic molecule and binds to a haptenic piperidinium cation having a quaternary nitrogen substituted with said migratory substituent or an analog thereof.

2. The antibody molecules or molecules containing antibody combining site portions of claim 1 wherein:

said blocked aromatic molecule is a cyclohexadienone having disubstituents at the para position, at least one of said disubstituents being said migratory substituent.

3. The antibody molecules or molecules containing antibody combining site portions of claim 1 wherein:

said migratory substituent is a benzyl substituent.

4. The molecules of claim 1 what are secreted by hybridoma 62C7 having ATCC accession number HB11703.

5. Cells that when cultured in a medium produce monoclonal antibody molecules or molecules containing antibody combining site portions that catalyze a dienone-phenol rearrangement reaction, the antibody combining site of said molecules bind to a cyclohexadienone substrate having disubstituents at the para position and bind to a haptenic piperidinium cation having a quaternary nitrogen substituted with said disubstituents or analogs thereof.

6. The cells of claim 5 that further secrete into the culture medium said monoclonal antibody molecules or molecules containing antibody combining site portions that catalyze a dienone-phenol rearrangement reaction.

7. The cells of claim 6 that are hybridoma cells.

8. Hybridoma cells of claim 7 that are those of hybridoma 62C7 having ATCC accession number HB11703.

9. A method of catalyzing a coupling of an aromatization of a blocked aromatic molecule with a sigmatropic shift of a migratory substituent on said blocked aromatic molecule, the method comprising the steps of:

Step A: admixing a catalytically effective amount of the monoclonal antibody molecules or molecules containing antibody combining site portions of claim 1 with said blocked aromatic molecule in an aqueous medium to form a reaction admixture; and then Step B: maintaining said reaction admixture of said Step A for a period of time sufficient for said antibody molecules or molecules containing antibody combining site portions to bind to said blocked aromatic molecule and to catalyze the coupling of the aromatization of said blocked aromatic molecule with a sigmatropic shift of a migratory substituent on said blocked aromatic molecule.

10. The method of claim 9 wherein said antibody molecules or molecules containing antibody combining site portions thereof are secreted by hybridoma 62C7 having ATCC accession number 11703.

11. A process for carrying out a dienone-phenol rearrangement reaction comprising the following steps:

Step A: in a aqueous medium at a pH value between about 5 and 8, forming a reaction mixture by admixing a cyclohexadienone substrate having disubstituents at the para position and a catalytically effective amount of monoclonal antibodies or paratope-containing portions of said monoclonal antibodies, wherein said monoclonal antibodies or paratope-containing portions thereof bind to said substrate and also bind to a piperidinium hapten having a charged ring nitrogen bonded to disubstituents substantially equivalent to said disubstituents at the para position of said substrate; and then Step B: maintaining said reaction mixture under biological reaction conditions for a time period sufficient for said substrate to undergo the dienone-phenol rearrangement reaction.

12. A method of preparing cells that when cultured in a medium produce antibody molecules or molecules containing antibody combining site portions that catalyze a coupling of an aromatization of a blocked aromatic molecule with a sigmatropic shift of a migratory substituent on said blocked aromatic molecule, the method comprising the steps of:

Step A: immunizing an animal with an immunogen that includes a piperidinium cation having a quaternary nitrogen having disubstitutions, at least one of said disubstitutions being said migratory substituent or an analog thereof; then Step B: maintaining said animal for a time period sufficient for said animal to secrete antibodies that immunoreact with said haptenic ligand; then Step C: transferring genes that encode antibody molecules or molecules containing antibody combining site portions from antibody-producing cells of said maintained, immunized animal of step (b) into host cells to form hybrid cells that contain genes from at least two sources, and which formed hybrid cells (i) produce antibody molecules or molecules containing antibody combining site portions from said transferred genes when cultured and (ii) can be cultured substantially indefinitely; then Step D: culturing the hybrid cells in as appropriate culture medium for a time period sufficient for those hybrid cells to produce antibody molecules or molecules containing antibody combining site portions; then Step E: recovering antibody molecules or molecules containing antibody combining site portions from the cultured hybrid cells; then Step F: screening the obtained antibody molecules or molecules containing antibody combining site portions that catalyze the coupling of an aromatization of a blocked aromatic molecule with a sigmatropic shift of a migratory substituent on said blocked aromatic molecule; and then Step G: growing clones of said identified hybrid cell that produces antibody molecules or molecules containing antibody combining site portions that catalyze the coupling of the aromatization of said blocked aromatic molecule with the sigmatropic shift of the migratory substituent on said blocked aromatic molecule.

13. The method of claim 12 wherein the cells formed in said Step C are hybridoma cells.

* * * * *